United States Patent [19]

Neti et al.

[11] 4,372,915
[45] Feb. 8, 1983

[54] FLUORESCENT SULFUR DIOXIDE ANALYZER HAVING AN IMPROVED SULFUR DIOXIDE GENERATOR

[75] Inventors: Radhakrishna M. Neti, Brea; Raymond E. Rocks, Anaheim, both of Calif.

[73] Assignee: Beckman Instruments, Inc., Fullerton, Calif.

[21] Appl. No.: 277,458

[22] Filed: Jun. 26, 1981

[51] Int. Cl.³ .......................... G01N 21/64; B01J 7/00
[52] U.S. Cl. ...................................... 422/91; 250/373; 356/417; 422/52; 422/186; 423/542; 436/122
[58] Field of Search ............................. 422/90, 91, 52; 23/232 R; 204/157.1 R; 356/317, 318, 243, 417; 250/373; 423/542

[56] References Cited

U.S. PATENT DOCUMENTS

| | | | |
|---|---|---|---|
| 1,969,655 | 8/1934 | Mailey | 204/157.1 R |
| 4,045,316 | 8/1977 | Legan | 204/157.1 R |
| 4,077,774 | 3/1978 | Neti et al. | 422/52 |
| 4,087,342 | 5/1978 | Bloomfield | 204/157.1 R |
| 4,189,363 | 2/1980 | Beitzel | 204/157.1 R |

OTHER PUBLICATIONS

CA 31:2517(2), Invisible Radiations in Gaseous Reactions, Jablczynski et al.

Primary Examiner—Michael S. Marcus
Attorney, Agent, or Firm—R. J. Steinmeyer; P. R. Harder; Edward C. Jason

[57] ABSTRACT

A fluorescent sulfur dioxide analyzer that includes a generator for producing a standard gas of known sulfur dioxide content. A source of ultraviolet radiation illuminates the interior of a reaction chamber in which an oxygen containing gas is passed over a deposit of sulfur. During passage, a part of the oxygen reacts with the sulfur to produce sulfur dioxide. Because the quantity of sulfur dioxide is predictable and reproducible, the resulting sulfur dioxide containing gas is suitable for use as a standard or span gas in the analyzer with which it is used, thereby eliminating the need for the storage tanks or permeation tubes.

9 Claims, 8 Drawing Figures

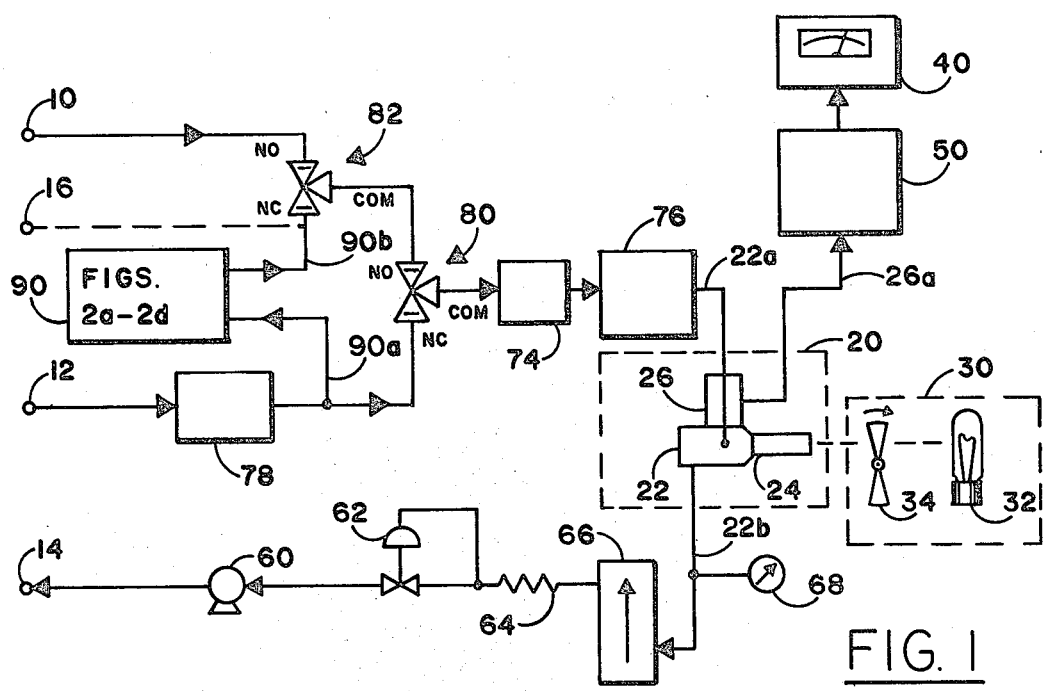
FIG. 1
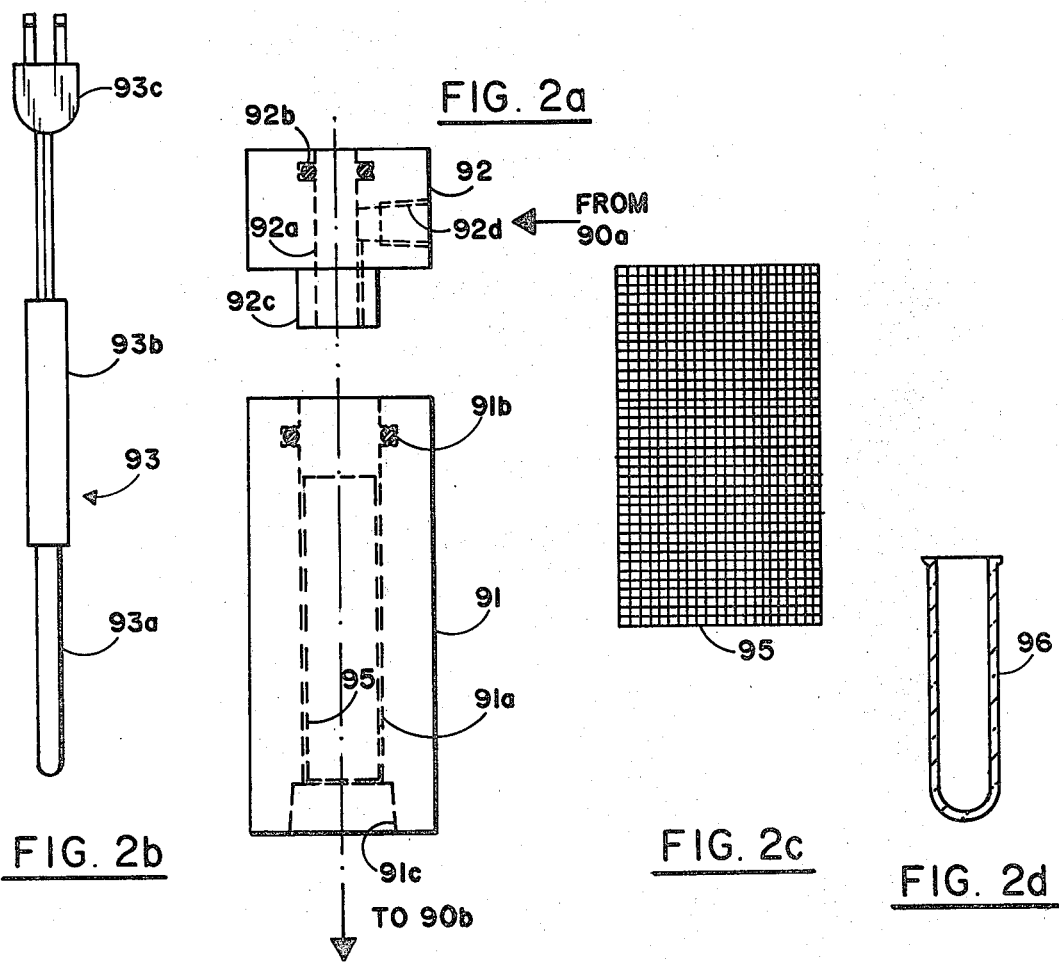
FIG. 2a
FIG. 2b
FIG. 2c
FIG. 2d

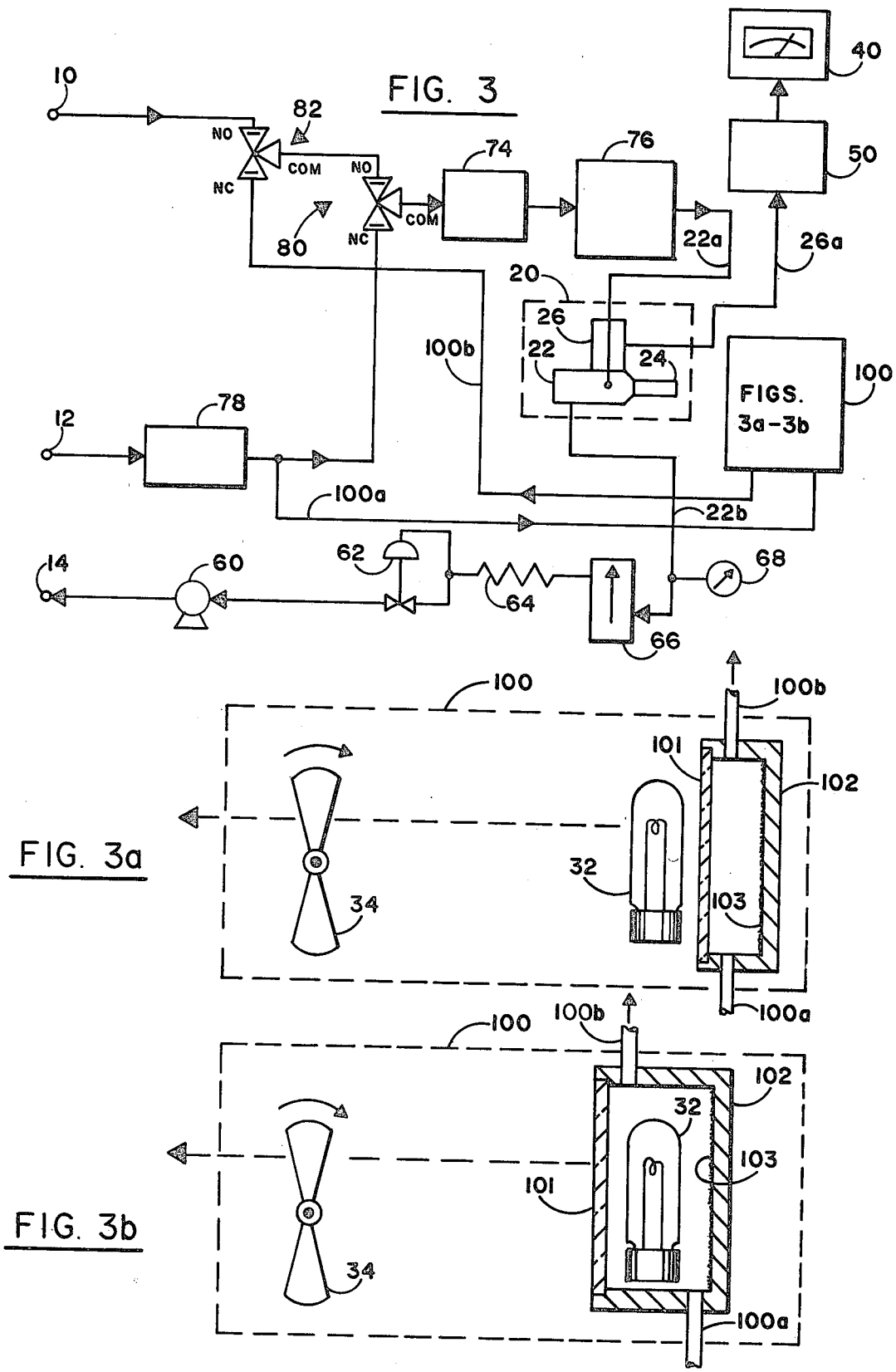

FLUORESCENT SULFUR DIOXIDE ANALYZER HAVING AN IMPROVED SULFUR DIOXIDE GENERATOR

BACKGROUND OF THE INVENTION

The present invention relates to sulfur dioxide analyzers and, more particularly, to an improved sulfur dioxide analyzer having a generator for generating a sulfur dioxide containing standard gas from elemental sulfur.

In measuring the sulfur dioxide content of a sample gas of unknown composition, one widely used technique involves measuring the quantity of fluorescent radiation emitted by the same gas at wavelengths that are known to be characteristic of sulfur dioxide. This fluorescence is ordinarily stimulated by illuminating the sample gas with ultraviolet radiation through a first band pass filter having a pass band calculated to selectively excite sulfur dioxide molecules. The fluorescent radiation emitted by these excited sulfur dioxide molecules is then ordinarily measured with a photomultiplier tube that is exposed to the sample gas through a second band pass filter having a pass band corresponding to the frequency of sulfur dioxide fluorescence.

In calibrating sulfur dioxide analyzers of the above-described type, it has been the practice to supply the analyzer with a standard or span gas of known sulfur dioxide content from sources of one of two types. One type of source includes external storage tank of a compressed sulfur dioxide containing gas of known composition. While this arrangement operated satisfactorily, it has associated with it the expense and inconvenience of obtaining, installing, and maintaining a storage tank for compressed gas. As is well known, such tanks are bulky, heavy and subject to leakage.

Another type of source for the sulfur dioxide containing standard gas includes permeation tubes. The latter tubes typically comprise a body of porous material which has been impregnated with sulfur dioxide, and which is designed to gradually release the sulfur dioxide into a gas stream that is caused to flow thereover. While permeation tubes are convenient and inexpensive, they are also subject to problems that render their use unattractive. A major one of these is the relatively short time within which the permeation tube becomes functionally exhausted, i.e., provides a gas stream with less than the required quantity of sulfur dioxide. As a result, the use of permeation tubes under any but the most closely monitored conditions can lead to a progressive loss in the accuracy of the calibration upon which all operational measurements are based.

Another problem with permeation tubes is the instability of their sulfur dioxide output. As is well known, permeation tubes are sensitive to changes in temperature, humidity and gas flow rate. Since a given set of these conditions may not be accurately reproducible during successive calibrations, the data obtained after such calibrations may include differences not related to differences in the sulfur dioxide content of the sample gas. Thus, the use of permeation tubes can result in measurements containing significant errors.

SUMMARY OF THE INVENTION

In accordance with the present invention, there is provided a convenient, long lasting and stable sulfur dioxide generator for use in fluorescent sulfur dioxide analyzers. In the preferred embodiment, the sulfur dioxide generator is included as an integral part of the fluorescent analyzer with which it operates, the combined generator-analyzer comprising an improved, self-contained analyzer which has improved calibration characteristics, and yet which requires no external source of sulfur dioxide. The advantages of the present invention may, however, also be provided by using the sulfur dioxide generator of the invention as an accessory, which can be used to retrofit existing sulfur dioxide analyzers to eliminate the need for the storage tanks or permeation tubes normally used in connection therewith.

As will be explained more fully hereinafter, the sulfur dioxide standard gas generator of the invention produces the desired sulfur dioxide by applying ultraviolet light to a reaction chamber through which a stream of an oxygen containing gas is directed over a deposit of elemental sulfur or other suitable sulfur containing material. This action may be produced by a variety of physical structures. The ultraviolet source, oxygen containing gas and sulfur may, for example, but brought together in the interior of a reaction chamber in which the oxygen containing gas flows between the ultraviolet source and the sulfur deposit. On the other hand, the ultraviolet source may be external to the reaction chamber with the oxygen containing gas and the sulfur deposit being illuminated by the ultraviolet source through an ultraviolet-transparent sidewall of the reaction chamber. In addition, the sulfur deposit may be formed in any of a variety of convenient ways. The sulfur deposit may, for example, comprise a sulfur coating on a metal screen that has been dipped into and withdrawn from molten sulfur. The desired sulfur deposit may also be formed by deposition from the vapor or liquid phase, or may even be cast from liquid sulfur or machined from solid sulfur. These embodiments, among others, will be described more fully presently.

In accordance with still another feature of the present invention, the ultraviolet source used in the sulfur dioxide generator of the invention may be the same as or different from the ultraviolet source that is used to excite the sample gas in the sulfur dioxide detecting assembly. More particularly, a first ultraviolet source may be used as a part of the sulfur dioxide generator, while a second ultraviolet source serves as the fluorescent exciting source for the fluorescent sulfur dioxide detecting assembly. On the other hand, the analyzer of the invention may be constructed so that a single ultraviolet source serves both of these functions. As a result, the sulfur dioxide generator of the invention may be provided either as an integral part of a newly designed analyzer, by adopting the latter configuration, or may be provided as a retrofit assembly for existing analyzers, by adopting the former configuration. It will be understood that both approaches are within the contemplation of the present invention.

DESCRIPTION OF THE DRAWINGS

FIG. 1 is a block diagram of a fluorescent sulfur dioxide analyzer constructed in accordance with the present invention.

FIGS. 2a–2d illustrate the components of the sulfur dioxide generator shown in block form in FIG. 1, FIG. 3 is a block diagram of an alternative embodiment of a fluorescent sulfur dioxide analyzer constructed in accordance with the present invention, and FIGS. 3a and 3b show the structural detail of two embodiments of the sulfur dioxide generator shown in block form in FIG. 3.

DESCRIPTION OF THE PREFERRED EMBODIMENTS

Referring to FIG. 1, there is shown one embodiment of a fluorescent sulfur dioxide analyzer that has been constructed in accordance with the invention. The analyzer of FIG. 1 includes a sample gas inlet 10 for connection to a source of the gas that is to be analyzed, a zero gas inlet 12 for connection to a source of zero gas which is or can be made free of sulfur dioxide, and an outlet 14 through which the gas passing through the analyzer may be eliminated after the analysis thereof is complete. Within the analyzer of FIG. 1 the concentration of sulfur dioxide is measured in a fluorescent detecting assembly 20 which is supplied with ultraviolet (UV) exciting radiation from a suitable ultraviolet source assembly 30. The output signal produced by detecting assembly 20 during a measurement is communicated to the user by a suitable analog or digital display 40 after being processed by electronic display control network 50.

Fluorescent detecting assembly 20 preferably includes a sample cell or fluorescence chamber 22 which receives a flow of sample gas from sample inlet 10 through an inlet line 22a, and which vents that flow to outlet 14 through an outlet line 22b. Detecting assembly 20 also includes a collimator 24 which includes the lenses, slits and UV band pass filters which condition the UV exciting radiation from source assembly 30, in a well-known manner, prior to its application to sample cell 22. Finally, detecting assembly 20 includes a photomultiplier 26 which measures the intensity of the fluorescent radiation from the UV excited sulfur dioxide molecules in sample cell 22 and provides an output signal proportional thereto on output signal conductor 26a.

In order to assure that photomultiplier 26 supplies to display control network 50 a signal which reflects only fluorescent emissions from excited sulfur dioxide molecules, the axes of the photomultiplier 26 and collimator 24 are preferably positioned at right angles to one another. This prevents UV radiation from collimator 24 from being transmitted directly to photomultiplier 26. In addition, in order to reduce the effect of possible fluorescent emissions by interfering compounds in the sample gas, photomultiplier 26 is ordinarily exposed to the interior of sample cell 22 through a band pass filter having a pass band that substantially excludes radiation not associated with sulfur dioxide fluorescence. Because the structure and operation of detector assembly 20 and its components are well known to those skilled in the art, the structure and operation thereof will not be described in detail herein.

Source assembly 30 includes a conventional UV/visible lamp 32 which is arranged to supply UV exciting radiation to detecting assembly 20 through a rotating chopper blade 34 that is rotated by a conventional chopper motor (not shown). Chopper blade 34 interrupts the UV exciting radiation at approximately a 10 Hz rate to provide the periodic change in excitation intensity that is later used by electronic network 50 for noise reduction purposes. Because the structure and operation of lamp 32 and chopper 34 are known to those skilled in the art, the structure and operation thereof will not be further described herein.

To the end that the rate of flow of the sample gas through sample cell 22 may be set at a known value, outlet line 22b of sample cell 22 is connected to outlet 14 through a pump 60, an adjustable back pressure regulator 62, a flow restrictor or capillary 64, a flow rate indicator 66 and a pressure gauge 68. Pump 60 provides the driving pressure which causes sample gas to flow between inlet 10 and outlet 14 through sample cell 22. Pressure regulator 62 establishes a substantially constant pressure across sample cell 22 and, together with the substantially fixed flow resistance of capillary 64, causes sample gas to flow through detector assembly 20 at a substantially constant rate. Ordinarily, pressure regulator 62 is adjusted until the desired sample gas flow rate is indicated by flowmeter 66. Such adjustments are ordinarily made at the initial setup of the analyzer and are not changed thereafter. Since the flow control arrangement including elements 60–68 is known to those skilled in the art, the latter will not be further described herein.

To the end that compounds which interfere with sulfur dioxide measurements may be removed from the sample gas, the analyzer of FIG. 1 may be provided with a scrubber unit 74 and/or with a heated interferent reactor 76, which are preferably connected in series with the sample cell inlet line 22a. Scrubber unit 74 may, for example, comprise a tube packed with a mixture of mercuric chloride and polytetrafluoroethylene to remove hydrogen sulfide and mercaptans from the sample gas. Additionally, interferent reactor 76 may comprise a tube packed with vanadium pentoxide on an inert substrate to oxidize the aromatic hydrocarbons in the sample gas. Since, however, scrubber 74 and reactor 76 are not directly related to the present invention, they will not be described in detail herein.

During the calibration of the analyzer of FIG. 1, it is customary to adjust the zero of display 40 while sulfur-dioxide-free or zero gas is being supplied to sample cell 22 through inlet 12. This zero gas may, for example, comprise ambient air which has been passed through a sulfur dioxide scrubber 78 that has been packed with activated carbon. For convenience, the zero gas from inlet 12 may be applied to sample cell inlet line 22a through the normally closed path of a solenoid actuated three-way valve 80 that is located between scrubbers 74 and 78.

Prior to the present invention, it was the practice to adjust the span of the analyzer while sample cell 22 was being supplied with a standard or span gas of known sulfur dioxide content, through a standard gas inlet. The latter inlet, the need for which is eliminated by the present invention, is shown as element 16 in FIG. 1, together with a dotted line showing the connecting tubing that was associated therewith. In accordance with the present invention the desired standard gas is provided by a sulfur dioxide generator assembly 90, one embodiment of which is shown in disassembled form in FIGS. 2a–2d. As shown in FIG. 1, sulfur dioxide generator 90 is preferably connected between scrubber 78 and a valve 82 which will be described presently. It will be understood, however, that generator 90 may in general be connected in any manner in which it can receive an oxygen containing gas at its inlet and in which it can supply a sulfur dioxide containing standard gas to sample cell inlet line 22a. For the sake of convenience, the sulfur dioxide standard gas produced by generator 90 is preferably applied to sample cell inlet line 22a through the normally closed passage of a solenoid actuated three-way valve 82 which is connected as shown in FIG. 1.

After the zero and span have been adjusted, the analyzer of FIG. 1 is in condition to receive a sample gas of unknown composition through sample gas inlet 10. Sample gas flow through inlet 10 is established by causing solenoid valves 80 and 82 to both assume their normally open states to connect inlet 10 to sample cell inlet line 22a. During the latter condition, both sulfur dioxide generator 90 and inlet 12 are disconnected from line 22a. Because the electrical circuitry that controls the states of valves 80 and 82 are of a type that is well known to those skilled in the art, that circuitry will not be described herein.

To the end that sulfur dioxide generator 90 may provide the analyzer of FIG. 1 with the desired sulfur dioxide containing standard gas, generator 90 may include the elements shown in disassembled form in FIGS. 2a-2d. As shown in FIG. 2a, generator 90 includes a generally cylindrical two-piece plastic housing including sections 91 and 92. As shown in FIG. 2b, generator 90 also includes a suitable ultraviolet lamp 93, having a bulb portion 93a, a base portion 93b, and an electrical connecting plug 93c, which may be of the type that contains mercury. Lamp 93 may also, however, be of the type that contains hydrogen, deuterium, zinc or xenon, among others. Finally, generator 90 includes a screen 95, shown in FIG. 2c, upon which sulfur has been deposited, and a UV filter element 96, shown in FIG. 2d. As will be explained more fully presently, filter element 96 may be used to limit the UV radiation to which the sulfur deposit is exposed to any desired portion of the UV spectrum.

During assembly, the sulfur-coated screen 95 of FIG. 2c is wound into a generally cylindrical form and inserted into the central hole 91a through housing section 91. Next, filter element 96 of FIG. 2d is slid over the bulb portion 93a of lamp 93, until it comes to rest against the insulating base 93b thereof. The assembled lamp-filter 93-96 is then inserted into the central hole 92a through housing section 92 so that a substantially gas-tight seal is formed between the insulating base 93b of lamp 93 and the O-ring seal 92b that is mounted within housing section 92. Finally, the latter assemblage of elements is slid into central opening 91a of housing section 91 so that shoulder 92c of housing section 92 forms a substantially gas-tight seal with O-ring seal 91b of housing section 91.

When fully assembled in the above-described manner, sulfur dioxide generator 90 provides a convenient and compact cylindrical assembly having an inlet opening 92d for coupling to generator inlet line 90a of FIG. 1 and an outlet opening 91c for coupling to generator outlet line 90b of FIG. 1. Once these inlet and outlet connections are made and connector plug 93c is plugged into a suitable source of operating voltage, generator 90 will generate a sulfur dioxide containing gas as long as an oxygen containing gas flows therethrough.

The operation of sulfur dioxide generator 90 will now be described. As the oxygen containing zero gas enters generator inlet 92d, it is exposed to the sulfur deposited on screen 95 in the presence of UV radiation from lamp 93. Under steady state conditions, the temperature at which this exposure occurs is preferably approximately 75° C. Under these conditions some of the sulfur from the sulfur deposit is oxidized to sulfur dioxide, which is then swept along with the oxygen containing gas stream. In accordance with the present invention, both the quantity of sulfur dioxide that is introduced into the gas stream and the predictability of this quantity are such that the gas stream is satisfactory for use as the sulfur dioxide containing standard gas. In addition, it has been found that the desired sulfur dioxide concentration can be provided without any significant production of either ozone or sulfur trioxide.

The concentration of the sulfur dioxide in the gas stream at outlet 90b of generator 90 is a function of the rate at which gas flows through generator 90, the wavelength and intensity of the radiation from UV lamp 93, and the area of the sulfur deposit over which the oxygen containing inlet gas flows during exposure to UV radiation. If relatively high sulfur dioxide concentrations are desired, for example, such concentrations may be provided by causing gas to flow through generator 90 relatively slowly and to encounter a sulfur deposit having a relatively large area that is intensely illuminated by UV radiation. On the other hand, if the relatively low concentrations of sulfur dioxide are desired, such concentrations may be provided by (a) increasing the rate of flow of gas through generator 90, (b) decreasing the intensity of the UV radiation, or (c) decreasing the UV illuminated surface area of the sulfur deposit. Alternatively, if the UV illuminated area of the sulfur deposit is fixed, the concentration of sulfur dioxide may be controlled (a) by varying the operating power of UV lamp 93, while maintaining a fixed gas flow rate therethrough, (b) by varying the rate of flow of gas through generator 90 (as, for example, by placing one or more needle valves in series and/or parallel with generator 90), while maintaining a constant level of operating power to UV lamp 93, or (c) by varying both of these quantities simultaneously. It will be understood that all of these approaches to controlling the sulfur dioxide concentration of the sulfur dioxide standard gas are within the contemplation of the present invention.

As a specific example, with a mercury containing UV lamp operating at a voltage of 110 volts and a current of 7 milliamps, an oxygen containing gas stream comprising sulfur-dioxide-free ambient air flowing at a rate of 400 cc per minute, and a sulfur deposit covering the interior surface of a circular tube having an outside diameter of 11 millimeters and a length of 5.5 centimeters, the gas at the output of generator 90 had a concentration of 3.02 parts per million of sulfur dioxide. For conditions that were the same except for operating voltages of 90 volts and 70 volts, the sulfur dioxide concentrations were 2.16 and 1.58 parts per million, respectively. Concentrations of this order of magnitude are suitable for use in sulfur dioxide analyzers of the type used to make measurements on ambient air. Much larger concentrations may, of course, be generated for non-ambient type analyzers.

During a series of experiments, various types of UV filter elements of the type shown as element 96 in FIG. 2d were placed over bulb 93a to restrict the range of UV wavelengths with which lamp 93 illuminated the sulfur deposit. As a result of these experiments, it was found that the composition of filter element 96 had a significant effect on the quantity of sulfur dioxide produced. More particularly, the quantity of sulfur dioxide produced increased as filter 96 was changed to transmit UV wavelengths of shorter and shorter wavelengths. Thus, the use of differing types of filter elements provides an additional measure of control over the quantity of sulfur dioxide generated.

Representative results of experiments with different filter elements may be summarized as follows. A filter element 96 that was constructed of a borosilicate glass of the type often sold under the trademark "Pyrex," was found to produce a barely measurable quantity of sulfur dioxide. Such glasses are known to transmit little UV radiation shorter than 2537 angstroms. The use of a filter element of a high purity glass sold under the trademark "Vycor" (more particularly glass #7913 manufactured by Corning), resulted in the production of approximately 20 times the quantity of sulfur dioxide produced with the use of the previous filter. Such glass is known to transmit wavelengths shorter than 2537 angstroms, but not as short as 1849 angstroms, the threshold wavelength for ozone production. A filter constructed of fused quartz of the type sold under the trademark "Supracil" produced the highest quantity of sulfur dioxide, this quantity being almost twice that produced with the use of the last mentioned filter. Such glass is known to transmit wavelengths shorter than 1849 angstroms, but not as short as 1500 angstroms. In view of these results, it will be seen that generator 90 may be provided with a filter that, along with other factors, controls the level of sulfur dioxide production and that may be used to suppress wavelengths that may promote other, undesired chemical reactions within generator 90.

In a further set of experiments it has been found that the manner in which the sulfur is deposited or held in place within generator 90 has little effect on the successful practice of the present invention. Instead of being deposited by dipping screen 95 in molten sulfur, for example, the sulfur may be deposited directly on the interior surface of hole 91a in housing section 91. This deposition may be accomplished by condensation of sulfur from the vapor phase or precipitation from a suspension or solution of sulfur in carbon disulfide, carbon tetrachloride or a variety of other solvents. Moreover, housing section 91 itself may be composed of solid sulfur that has been cast from liquid sulfur or machined from solid sulfur. Finally, the sulfur may be present in the form of a mixture of sulfur with other compounds or even as a compound of sulfur which can be converted to sulfur dioxide in the presence of conditions existing within generator 90.

While the sulfur dioxide generator of FIGS. 2a–2d is shown in FIG. 1 as being included in the interior of the analyzer with which it is used, this location is not a necessary one. Generator 90 may, for example, be located outside of the analyzer housing so that its output 90b is connected to an existing standard gas coupling such as that labeled 16 in FIG. 1. Naturally, the latter event, it may be necessary to supply ambient air to generator input 90a through a separate $SO_2$ scrubber similar to scrubber 78 of FIG. 1. Thus, the present invention may be implemented by including generator 90 as an integral part of a new analyzer, or may be implemented by adding it as an accessory to an existing analyzer.

In order to provide a sulfur dioxide generator which produces sulfur dioxide in a stable manner over long periods of use, it is desirable that the sulfur deposit contain a sufficient quantity of sulfur so that the sulfur dioxide generation process not lead to the rapid exhaustion of the deposit. To this end it is preferred that the sulfur deposit be sufficiently thick that the consumption of sulfur at the surface thereof merely exposes fresh sulfur which then continues to support the operation of the sulfur dioxide generator in place of the original sulfur. In general, however, the sulfur deposit may be as thick or as thin as is considered desirable for a particular application.

Referring to FIG. 3, there is shown an alternative embodiment of the invention in which the UV radiation required by detecting assembly 20 and the UV radiation required by the sulfur dioxide generator of the invention are provided by a single UV lamp. The embodiment of FIG. 3 is generally similar to that of FIG. 1, like functioning parts being similarly numbered. The embodiment of FIG. 3 differs from that of FIG. 1, however, in that the embodiment of FIG. 3 includes a UV source-generator assembly 100 which serves both the function of source assembly 30 and the function of sulfur dioxide generator 90 of FIG. 1. To this end, UV source-generator assembly 100 is located so that the UV lamp contained therein may illuminate the end of collimator 24 of detecting assembly 20. At the same time, the UV lamp within assembly 100 is used as a part of a sulfur dioxide generator which is connected to the analyzer in the same manner as generator 90 of FIG. 1, through an inlet line 100a and an outlet line 100b. Two alternative internal structures for UV source assembly 100 are shown in FIGS. 3a and 3b.

Referring to FIG. 3a, it will be seen that combined UV source-generator assembly 100 includes UV lamp 32 which illuminates collimator 24 of detecting assembly 20, through chopper blade 34, in the manner described in connection with the embodiment of FIG. 1. At the same time, however, UV lamp 32 shines on a sulfur deposit 103, through a UV-transparent window 101, which corresponds to filter 96 of FIG. 2d. Together with housing member 102, window 101 forms an enclosure within which the desired sulfur dioxide is generated. As a result, when an oxygen containing (and $SO_2$ free) gas stream is introduced through inlet 100a the desired sulfur dioxide containing standard gas becomes available at outlet 100b. Thus, the assembly 100 of FIGS. 3 and 3a serves the functions of both the source assembly 30 and the sulfur dioxide generator 90 of FIG. 1.

Referring to FIG. 3b, there is shown an alternative embodiment for the combined source-generator assembly 100 of FIG. 3. The embodiment of FIG. 3b is generally similar to that of FIG. 3a, but differs therefrom in that UV lamp 32 is located inside of housing 102 rather than outside thereof. The sulfur dioxide generation process is similar for FIGS. 3a and 3b, however, since both embodiments bring together UV radiation from lamp 32, a sulfur deposit, and a flow of an oxygen containing gas. Nevertheless, the embodiment of FIG. 3b is not preferred over that of FIG. 3a. One reason is that the embodiment of FIG. 3b may require a UV transparent window 101 as well as a filter element corresponding to filter 96 of FIG. 2d. Another reason is that the presence of sulfur dioxide within enclosure 101-102 of FIG. 3b can absorb enough of the UV radiation from lamp 32 to adversely affect the excitation of $SO_2$ in sample cell 22. Thus, the source-generator assembly shown in FIG. 3b does not represent a preferred embodiment of the present invention.

In view of the foregoing, it will be seen that the present invention contemplates an improved fluorescent sulfur dioxide analyzer having a convenient, long lasting and stable source of sulfur dioxide containing standard gas. It will also be seen that the present invention contemplates a sulfur dioxide generator assembly which, although especially suited for including as an integral part of a fluorescent sulfur dioxide analyzer may also be added, as an accessory, to convert an existing sulfur dioxide analyzer to an analyzer which employs the present invention.

While the present invention has been described in relation to a number of specific embodiments, it will be understood that the true scope of the present invention should be determined with reference to the following claims.

What is claimed is:

1. In a fluorescent sulfur dioxide analyzer of the type having a fluorescence chamber and a detector for measuring fluorescent emissions from sulfur dioxide molecules in the fluorescence chamber, the improvement comprising:
   (a) a sulfur dioxide generator including:
      (i) means defining an enclosure having an inlet for connection to a source of an oxygen containing gas and an outlet;
      (ii) means defining a sulfur deposit within the enclosure;
      (iii) source means for producing ultraviolet radiation, said source means being arranged to illuminate the sulfur deposit while the oxygen containing gas flows thereover at a selected range of wavelengths to generate sulfur dioxide without also generating substantial amounts of ozone; and
   (b) means for connecting the sulfur dioxide generator in gas-supplying relationship to the fluorescence chamber.

2. The analyzer of claim 1 in which the oxygen containing gas is sulfur-dioxide-free air.

3. The analyzer of claim 1 in which the enclosure includes an ultraviolet transparent window, and in which the source means is outside of the enclosure and illuminates the interior thereof through said window.

4. The analyzer of claim 1 in which the radiation source means is located within the enclosure.

5. The analyzer of claim 1, 3 or 4 in which the radiation source means is positioned to provide ultraviolet radiation to the fluorescence chamber.

6. The analyzer of claim 1 in which the enclosure is fabricated from sulfur and in which at least one surface of said fabricated enclosure is said sulfur deposit.

7. The combination of a fluorescent sulfur dioxide analyzer and a sulfur dioxide containing standard gas generator, said standard gas generator including:
   (a) means defining a sulfur deposit,
   (b) means associated with said standard gas generator for supporting said sulfur deposit
   (c) means for directing a flow of an oxygen containing gas over the sulfur deposit,
   (d) a source of ultraviolet radiation for illuminating the sulfur deposit through the oxygen containing gas at a selected range of wavelengths to generate sulfur dioxide without also generating appreciable amounts of ozone; and
   (e) means for conveying the oxygen containing gas to the analyzer after exposure to the sulfur deposit and ultraviolet radiation.

8. The combination of claim 7 in which the analyzer includes a fluorescence chamber and in which the ultraviolet source applies a part of its ultraviolet radiation to the fluorescence chamber.

9. The combination of claim 7 in which the ultraviolet source is of the type which provides a substantial proportion of its ultraviolet output at wavelengths shorter than 2537 angstroms, but not shorter than 1849 angstroms.

* * * * *